United States Patent [19]

Miller

[11] Patent Number: 4,654,450

[45] Date of Patent: Mar. 31, 1987

[54] INHIBITING POLYMERIZATION OF VINYL AROMATIC MONOMERS

[75] Inventor: Richard F. Miller, Humble, Tex.

[73] Assignee: Atlantic Richfield Company, Los Angeles, Calif.

[21] Appl. No.: 832,496

[22] Filed: Feb. 24, 1986

[51] Int. Cl.[4] .................................................. C07C 7/20
[52] U.S. Cl. ................................. 585/5; 208/48 AA; 252/403; 252/405; 252/406; 585/435; 585/440; 585/864; 585/866; 585/952
[58] Field of Search .................. 585/2, 3, 4, 5, 856, 585/864, 865, 866, 952, 435, 440; 252/403, 404, 405, 406; 208/48 AA

[56] References Cited

U.S. PATENT DOCUMENTS

| | | | |
|---|---|---|---|
| 2,965,685 | 12/1960 | Campbell | 585/4 |
| 3,392,204 | 7/1968 | Albert | 585/4 |
| 4,400,625 | 8/1983 | Hussey | 307/66 |
| 4,409,408 | 10/1983 | Miller | 585/4 |
| 4,431,514 | 2/1984 | Fern | 208/48 AA |
| 4,440,625 | 4/1984 | Go et al. | 208/48 AA |
| 4,456,526 | 6/1984 | Miller et al. | 208/48 AA |
| 4,551,226 | 11/1985 | Fern | 208/48 AA |

*Primary Examiner*—Asok Pal
*Attorney, Agent, or Firm*—Coleman R. Reap

[57] ABSTRACT

Vinyl aromatic compounds are stabilized against undesired polymerization by adding to the vinyl aromatic compounds small amounts of a N,N-dialkylhydroxylamine and an alkyl benzene sulfonic acid.

11 Claims, No Drawings

4,654,450

INHIBITING POLYMERIZATION OF VINYL AROMATIC MONOMERS

FIELD OF THE INVENTION

The present invention relates the the stabilization of ethylenically unsaturated compounds and more particularly to the inhibition of undesired polymerization of vinyl aromatic compounds during storage, shipping or processing.

BACKGROUND OF THE INVENTION

Vinyl aromatic compounds such as styrene undergo undesired spontaneous polymerization (i.e. polymerization of monomers due to heat or the random generation of free radicals in the monomers) during storage, shipping or processing. The problem is particularly acute during purification operations carried out at elevated temperatures such as distillation. Spontaneous polymerization is disadvantageous not only because it causes fouling of distillation column reboilers and other equipment used for processing the vinyl aromatic monomer, but also because it usually renders the monomer unfit for use without further treatment. Accordingly, it is desirable and often necessary to inhibit the spontaneous polymerization of vinyl aromatic monomers.

PRIOR ART

To prevent spontaneous polymerization of vinyl aromatic monomers it is common practice to add to the monomers compounds which have polymerization inhibiting activity. A wide variety of such compounds, known as polymerization inhibitors, have been used for this purpose. Sulfur has been widely used in the past to inhibit polymerization of vinyl aromatic compounds. However, sulfur usage is undesirable because large quantities of sulfur are required for effective polymerization inhibition. This presents a waste removal problem when the monomer is separated from the sulfur-monomer mixture, which is accomplished by distillation. The distillation bottoms product, which contains higher molecular weight hydrocarbons, polymer and sulfur, cannot be burned due to the air pollution hazard caused by sulfur oxides. Thus, this material must be disposed of by burial in a waste dump.

In recent times, many chemical compounds have been developed as substitutes for sulfur in polymerization inhibiting applications. These compounds have been used as polymerization inhibitors for vinyl aromatic monomers with varying degrees of success. U.S. Pat. No. 3,390,198, issued to Leston, discloses the use of several mono and dialkylcatechols as polymerization inhibitors for hot styrene. U.S. Pat. No. 3,148,225, issued to Albert, employs dialkylhydroxylamines for inhibiting popcorn polymer formation in styrene-butadiene rubbers. The dialkylhydroxylamine compounds appear to react with and terminate free radicals which cause undesired formation of polymers. U.S. Pat. No. 2,965,685, issued to Campbell, discloses inhibiting polymerization by adding about 5 ppm to 5 percent dialkylhydroxylamine to styrene monomer. Sato et al, in U.S. Pat. No. 3,849,498, teach the use of diethylhydroxylamine as a polymerization inhibitor for an alcoholic solution of unsaturated aldehydes. MayerMader et al, U.S. Pat. No. 3,878,181, employ diethylhydroxylamine either alone or in combination with a water-soluble amine such as triethanolamine to terminate the aqueous emulsion polymerization of chloroprene. U.S. Pat. No. 4,440,625 discloses the use of mixtures of N,N-dialkylhydroxylamines and alkyl benzene sulfonic acids to inhibit fouling in petroleum processing equipment. U.S. Pat. No. 4,425,223 discloses the use of mixtures of alkyl benzene sulfonic acids and alkyl esters of a phosphonic acid to protect hydrocarbon processing equipment against fouling.

A major limitation attending the use of some dialkylhydroxylamines is that they have high partition coefficients. For example, N,N-diethylhydroxylamine has a 13:1 partition coefficient in favor of water. In other words, if a polymerization monomer, such as styrene, containing diethylhydroxylamine as a polymerization inhibitor is contacted with water, up to about 93% of the diethylhydroxylamine may be extracted from the monomer phase under equilibrium conditions. Thus, this compound is not always suitable as a polymerization inhibitor in actual manufacturing or storage operation where water may be used as a water wash or where water may accumulate in storage tank bottoms.

It has now been discovered that mixtures of N,N-dialkylhydroxylamines and alkyl benzene sulfonic acids provide outstanding polymerization inhibiting activity for vinyl aromatic monomers. Thus, because of the increased hydrocarbon solubility of these mixtures it is now possible to provide better overall polymerization inhibiting protection with mixtures of N,N-dialkylhydroxylamines and alkyl benzene sulfonic acids than is obtainable by the use of equivalent amounts of either of these groups of compounds by themselves.

Accordingly, it is object of the invention to present stable compositions of vinyl aromatic monomers. It is another object of the invention to present a method of effectively and economically inhibiting spontaneous polymerization of styrene and other vinyl aromatic monomers which may come into contact with water. These and other objects of the invention are supported in the following description and examples of the invention.

SUMMARY OF THE INVENTION

According to the invention the protection of vinyl aromatic monomers against spontaneous polymerization is accomplished by incorporating into the monomers mixtures of one or more dialkylhydroxlamines, each alkyl group of which has 2 to 10 carbon atoms, and one or more alkyl benzene sulfonic acids, the alkyl group of which has 1 to 20 carbon atoms.

DETAILED DESCRIPTION OF THE INVENTION

The term vinyl aromatic monomer, as used in this description, includes any of the readily polymerizable vinyl aromatic compounds, e.g. styrene, alpha alkyl styrene, such as alpha methyl styrene, ring alkyl substituted styrene such as p-methyl styrene, diethylenically substituted benzene compounds, such as divinylbenzene, etc. and mixtures thereof.

The N,N-dialkylhydroxylamine compounds used in the invention have the structural formula

wherein R and R' are the same or different straight or branced-chain alkyl groups having 2 to about 10, and preferably 2 to 6, carbon atoms. Although N,N-dialkylhydroxlamines having more than about 10 carbon atoms in each alkyl group may be useful in the invention it is preferred that compounds containing 10 or fewer carbon atoms in each alkyl group be used in the invention because the latter compounds are commercially available. Mixtures of two or more N,N-dialkylhydroxylamines can also be advantageously used in the compositions of the invention.

Suitable N,N-dialkylhydroxylamines include N,N-diethylhydroxylamine, N,N-dibutylhydroxylamine, N,N-butylethylhydroxylamine, N,N-didecylhydroxylamine, N,N-2-ethylbutyloctylhydroxylamine, etc. Examples of preferred N,N-dialkylhydroxylamines include N,N-diethylhydroxylamine and N,N-dibutylhydroxylamine. As noted above, two or more of these compounds may be used in combination, if desired.

Alkyl benzene sulfonic acid compounds useful in the invention are those having the structural formula

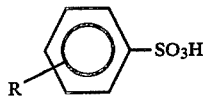

wherein R is an alkyl group having 1 to 20 or more carbon atoms. The total number of carbon atoms in R may exceed 20 but no particular advantage is derived from the use of such high molecular weight compounds. The alkyl groups may be straight or branched-chain. Preferred alkyl benzene sulfonic acids are those in which the total number of carbon atoms in R is 1 to 12. Mixtures of two or more alkyl benzene sulfonic acids may be used in the invention if desired.

Suitable alkyl benzene sulfonic acids include p-toluene sulfonic acid, p-dodecyl benzene sulfonic acid, p-t-butyl benzene sulfonic acid, p-t-amyl benzene sulfonic acid etc. Preferred alkyl benzene sulfonic acids include p-toluene sulfonic acid, p-dodecyl benzene sulfonic acid, etc.

Some N,N-dialkylhydroxylamines, such as N,N-diethylhyroxylamine, and some alkyl benzene sulfonic acids, such as p-dodecyl benzene sulfonic acid are available commercially. Those N,N-dialkylhydroxylamines and alkyl benzene sulfonic acids which are not commercially available may be prepared by any of the well know techniques. The preparation of these compounds forms no part of the present invention.

The relative concentrations of N,N-dialkylhydroxylamine and alkyl benzene sulfonic acid used in the invention are generally in the range of about 10 to 90 weight percent N,N-dialkylhydroxylamine and 90 to 10 weight percent alkyl benzene sulfonic acid, based on the total combined weight of these components. In preferred embodiments the concentrations generally fall in the range of about 25 to 75 weight percent N,N-dialkylhydroxylamine and 75-25 weight percent alkyl benzene sulfonic acid, based on the total combined weight of these components.

The polymerization inhibiting compositions of the invention are well suited for protecting the reboiler sections of a distillation column during distillation of vinyl aromatic monomers because of the high boiling point of these inhibitor compounds. They may be used at temperatures up to about 150° C. or higher at atmospheric pressure. To make up for the inhibitor which is left behind during distillation, additional inhibitor can be added to the vinyl aromatic monomer after it is distilled from heavier hydrocarbons. In some cases it may be desirable to use lower boiling polymerization inhibitors in combination with the inhibitor compositions of the invention. For example, when distilling a vinyl aromatic monomer from higher boiling hydrocarbons it may be advantageous to add a polymerization inhibitor which has a boiling point near or lower than the boiling point of the vinyl aromatic compound. This will provide protection to the overhead portion of the column. It may also be desirable to add with the polymerization inhibitor compositions of the invention other agents, such as corrosion inhibitors, to provide additional protection to process equipment.

The polymerization inhibitor compositions of the invention can be introduced into the monomer to be protected by any conventional method. It is generally introduced just upstream of the point of desired application by any suitable means, such as by the use of a proportionating pump. The polymerization inhibitor composition may be added as a concentrate but it is preferable to add it as a solution which is compatible with the monomer being treated. Suitable solvents include kerosene, naphtha, the lower alkanes such as hexane, aromatic solvents, such as toluene, alcohols, polyols, ketones, etc. It is often preferable to dissolve the inhibitors of the invention in the monomer to which the inhibitor is being added to avoid introducing additional impurities to the monomer. The concentration of polymerization inhibitor in the solvent is desirably in the range of about 1 to 30 weight percent and preferably about 5 to 20 weight percent based on the total weight of inhibitor and solvent.

The polymerization inhibitor is used at a concentration which is effective to provide the desired protection against spontaneous polymerization. It has been determined that amounts of polymerization inhibitor in the range of about 0.5 to 1000 ppm based on the weight of the monomer being treated affords ample protection against undesired polymerization. For most applications the inhibitor is used in amounts in the range of about 5 to 700 ppm.

The following examples will serve to further illustrate the invention. Unless otherwise stated, parts and percentages are on a weight basis. In the examples styrene, which is representative of vinyl aromatic monomers, was used as the test monomer. In the tests sodium ion, in the form of sodium hydroxide, and benzoyl peroxide were added to the test samples to provide a more intensive test of the ability of the inhibitor compositions of the invention to inhibit spontaneous polymerization. Sodium ions and benzoyl peroxide are both known addition polymerization catalysts for vinyl aromatic monomers.

EXAMPLE I (Control)

To distilled styrene was added sufficient sodium hydroxide (as a 50% aqueous solution) to produce a mixture containing 17 mg of sodium hydroxide per each 1000 grams of styrene monomer. This concentration of sodium hydroxide in the monomer is equivalent to a sodium ion concentration of 10 ppm. One hundred grams of the styrene monomer mixture was introduced into a 250 ml Erlenmeyer flask fitted with a ground glass stopper. Two hundred ppm, based on the weight of styrene, of benzoyl peroxide was added to the flask and the flask was then purged of air by bubbling nitrogen gas through the monomer. After the nitrogen purge the ground glass stopper was inserted into the flask and the flask was placed in an oven. The temperature of the oven was raised to and maintained at a temperature of 90±2° C. for the duration of the test. Ten ml samples were drawn from the flask every 30 minutes over a two hour period. The samples were carefully drawn under a nitrogen blanket to ensure that no atmospheric air entered the flask.

Each sample was tested to determine the amount of styrene polymer formed by the following procedure: The 10 ml sample of styrene monomer was introduced into 100 ml of cold methanol, thereby quenching the polymerization reaction. The methanol-monomer mixture was heated sufficiently to coagulate the polymer formed. The polymer was recovered from the methanol by filtration, dried overnight at a temperature of 100° F. and weighed. The percentage of polymer formed was determined and reported in the table in the Run 1 row.

EXAMPLE II (Comparative)

The procedure and tests of Example I were repeated except that 550 ppm of p-dodecylbenzene sulfonic acid was added to the Erlenmeyer flask just prior to the initial nitrogen purge. The styrene monomer was periodically tested as indicated in Example I. The results are tabulated in the table in the Run 2 row.

EXAMPLE III (Comparative)

The procedure and tests of Example II were repeated except that 150 ppm of diethylhydroxylamine was substituted for the p-dodecylbenzene sulfonic acid. The results are tabulated in the Table in the Run 3 row.

EXAMPLE IV (Comparative)

The procedure and tests of Example II were repeated except that 150 ppm of dietheylthydroxylamine was added to the styrene monomer and the resultant inhibited mixture was water washed with 10 volume percent of a 0.5 weight percent sodium hydroxide solution. The resulting water and styrene phases were separated and the styrene monomer was then tested as previously described. The results are tabulated in the table in the Run 4 run.

EXAMPLE V

The procedure and tests of Example IV were repeated except that 200 ppm of a mixture of diethylhydroxylamine (43 ppm) and p-dodecyl benzene sulfonic acid (157 ppm) was used as the inhibitor system. The results are tabulated in the Run 5 row of the table.

EXAMPLE VI

The procedure and tests of Example V were repeated except that 700 ppm of a mixture of diethylhydroxylamine (150 ppm) and p-dodecyl benzene sulfonic acid (550 ppm) was used as the inhibitor system. The results are tabulated in the Run 6 row of the table.

TABLE

| Run | Inhibitor | Inhibitor Concentration, ppm | Weight % Polymer Formed Time Min. | | | |
|---|---|---|---|---|---|---|
| | | | 30 | 60 | 90 | 120 |
| 1 | None | — | 0.22 | 1.28 | 2.74 | 5.37 |
| 2 | p-dodecyl benzene sulfonic acid | 550 | 0.27 | 1.35 | 2.70 | 5.04 |
| 3 | diethylhydroxylamine | 150 | 0.08 | 0.19 | 0.53 | 2.30 |
| 4 | diethylhydroxylamine | 150 | 0.30 | 0.87 | 2.62 | 4.84 |
| 5 | diethylhydroxylamine p-dodecyl benzene sulfonic acid | 43 157 | 0 | 0 | 0 | 2.62 |
| 6 | diethylhydroxylamine p-dodecyl benzene sulfonic acid | 150 550 | 0.07 | 0.10 | 0.166 | 0.25 |

The benefits of the use of the polymerization inhibitor compositions of the invention are shown in the table. In the table the uninhibited monomer contained 5.37 percent polymer after two hours; the two hour anaylsis of the Run 2 and Run 3 samples, which each contained one of the components of the inhibitor system of the invention, showed polymer concentrations of 5.04% and 2.30% respectively; the two hour analysis of the Run 4 sample, which contained one of the components of the inhibitor system of the invention and was water-washed, showed a polymer concentration of 4.84%. Thus, when a styrene sample containing an efficient polymerization inhibitor (diethylhydroxylamine) was water-washed it lost most of its inhibition. On the other hand, when a styrene sample containing the inhibitor system of the invention was water-washed and tested (Run 5) the inhibitor system remained active. Example 6 shows that when higher amounts of the inhibitor system of the invention are used the styrene remains inhibited to a much greater extent, even though the sample is water-washed.

Although the invention is described with particular reference to specific examples, it is understood that the invention includes obvious variants. For example, dialkylhydroxylamines other than diethylhydroxylamine can be used in the invention and the inhibitor system can be formulated to contain more than one member from each of the two specified classes of compounds. The scope of the invention is limited only by the breadth of the appended claims.

What is claimed is:

1. A composition comprised of (a) a vinyl aromatic compound containing an amount effective to inhibit polymerization of said vinyl aromatic compound of a mixture of (1) about 10 to 90 parts by weight of at least one N,N-dialkylhydroxylamine having identical or different alkyl groups each having 2 to 10 carbon atoms, and (2) about 90 to 10 parts by weight of at least one alkyl benzene sulfonic acid having 1 to 20 carbon atoms.

2. The composition of claim 1 wherein the total concentration of said mixture of N,N-dialkylhydroxylamine and alkyl benzene sulfonic acid in said composition is 0.5 to 1000 ppm, based on the total weight of vinyl aromatic compound.

3. The composition of claim 1 wherein the vinyl aromatic compound is styrene or alkyl substituted styrene, each alkyl group in (1) has 2 to 6 carbon atoms, the tertiary alkyl group in (2) has 4 to 8 carbon atoms, the relative concentrations of the compounds in (1) and (2) are 25 to 75 parts by weight and 75 to 25 parts by weight respectively and the total concentration of said mixture of N,N-dialkylhydroxylamine and alkyl benzene sulfonic acid is said composition is about 5 to about 700 ppm, based on the total weight of vinyl aromatic compound.

4. The composition of claim 3 wherein the vinyl aromatic compound is styrene, the compound in (1) is N,N-diethylhydroxylamine and the compound in (2) is p-toluene sulfonic acid.

5. The composition of claim 3 wherein the vinyl aromatic compound is styrene, the compound in (1) is N,N-diethylhydroxylamine and the compound in (2) is p-dodecyl benzene sulfonic acid.

6. In a method of inhibiting polymerization of a vinyl aromatic compound comprising adding to the vinyl aromatic compound an amount of a polymerization inhibiting system effective to substantially reduce the rate of polymerization, the improvement comprising using as the system a combination of:
 (a) about 10 to 90 parts of at least one N,N-dialkylhydroxylamine having identical or different alkyl groups each having 2 to 10 carbon atoms, and
 (b) about 90 to 10 parts of at least alkyl benzene sulfonic acid having 1 to 20 alkyl carbon atoms per each 100 total parts by weight of the compounds in (a) and (b).

7. The improved method of claim 6 wherein said system is added to the vinyl aromatic compound in a concentration of about 0.5 to 1000 ppm, based on the weight of said vinyl aromatic compound.

8. The improved method of claim 6 wherein each alkyl group of the compound in (a) has 2 to 6 carbon atoms, the alkyl group of the compound in (b) has 1 to 12 carbon atoms and said system is added to the vinyl aromatic monomer in a concentration of about 5 to 700 ppm, based on the weight of said vinyl aromatic compound.

9. The improved method of claim 7 wherein the compound in (a) is N,N-diethylhydroxylamine and the compound in (b) is p-toluene sulfonic acid.

10. The improved method of claim 7 wherein the vinyl aromatic compound is styrene, the compound in (1) is N,N-diethylhydroxylamine and the compound in (2) is p-dodecyl benzene sulfonic acid.

11. The improved method of any of claims 6, 7, 8, or 9 wherein the compounds in (a) and (b) are present in amounts of about 25 to 75 parts and 75 to 25 parts by weight, respectively.

* * * * *